US008673363B2

(12) United States Patent
Reynolds

(10) Patent No.: US 8,673,363 B2
(45) Date of Patent: Mar. 18, 2014

(54) DENTAL MINERALIZATION

(75) Inventor: Eric Charles Reynolds, Carlton (AU)

(73) Assignee: The University of Melbourne, Parkville, Victoria (AU)

( * ) Notice: Subject to any disclaimer, the term of this patent is extended or adjusted under 35 U.S.C. 154(b) by 641 days.

(21) Appl. No.: 11/916,831

(22) PCT Filed: Jun. 7, 2006

(86) PCT No.: PCT/AU2006/000785
§ 371 (c)(1),
(2), (4) Date: Dec. 7, 2007

(87) PCT Pub. No.: WO2006/130913
PCT Pub. Date: Dec. 14, 2006

(65) Prior Publication Data
US 2008/0193557 A1  Aug. 14, 2008

(30) Foreign Application Priority Data

Jun. 7, 2005  (AU) .................................. 2005902961

(51) Int. Cl.
*A61K 33/42* (2006.01)
*A61P 43/00* (2006.01)

(52) U.S. Cl.
USPC .............................. 424/602; 426/660; 514/7

(58) Field of Classification Search
USPC ...................................................... 424/52, 57
See application file for complete search history.

(56) References Cited

U.S. PATENT DOCUMENTS

| 4,522,805 | A | 6/1985 | Gordon |
| 5,015,628 | A | 5/1991 | Reynolds |
| 6,056,930 | A | 5/2000 | Tung |
| 6,780,844 | B1 | 8/2004 | Reynolds |
| 7,312,193 | B2 | 12/2007 | Reynolds |
| 2002/0028251 | A1 | 3/2002 | Okay |
| 2005/0063922 | A1 | 3/2005 | Reynolds et al. |

FOREIGN PATENT DOCUMENTS

| EP | 0 786 245 A1 | 7/1997 |
| EP | 1 525 878 A1 | 4/2005 |
| JP | 8-143436 A | 6/1996 |
| JP | 10-290682 | 11/1998 |
| JP | 3742523 | 11/1999 |
| JP | 2004215521 | 8/2004 |
| WO | WO 87/07615 | 12/1987 |
| WO | WO 93/03707 A | 3/1993 |
| WO | WO 94/00146 A1 | 1/1994 |
| WO | WO 98/40406 | 9/1998 |
| WO | WO 00/57892 | 10/2000 |
| WO | WO01/44106 | 6/2001 |
| WO | WO 02/094204 | 11/2002 |
| WO | WO 03/059303 | 7/2003 |
| WO | WO 03/059304 | 7/2003 |
| WO | WO 2004/035077 | 4/2004 |
| WO | WO 2004/054531 | 7/2004 |
| WO | WO 2006/130913 A1 | 12/2006 |

OTHER PUBLICATIONS

Slomiany et al., "Salivary Mucins in Oral Mucosal Defense." Gen. Parmac. 1996:27(5);pp. 761-771.*
Perdigao et al., "Contemporary Trends and Techniques in Tooth Whitening." Practical Procedures & Aesthetic Dentistry 2004:16(3);185-192.*
"Colorimetry" Second Edition. By CIE Technical Committee. CIE 1986.
Aoba, T. et al. "Dental Fluorosis: Chemistry and Biology." Crit Rev Oral Biol Med. 13 (2) pp. 155-170 (2002).
DenBesten, P.K. et al "Biological Mechanisms of Fluorosis and Level and Timing of Systemic Exposure to Fluoride with Respect to Fluorosis." J. Dent Re 71(5): pp. 1238-1243 May 1992.
Birgit, Angmar D. "Studies on the Ultrastructure of Dental Enamel." J. Ultrastructure Research 8, (1963) pp. 12-23.
Black, G.V. et al. "Mottled Teeth" The Dental Cosmos. vol. LVIII. No. 2. Feb. 1916.
Fejerskov, O. et al. "The Nature of Mechanisms of Dental Fluorosis in Man." J Dent Res 69 (Spec Iss) Feb. 1990 pp. 692-700.
Fejerskov, Ole et al. "Posteruptive changes in human dental fluorosis—a histological and ultrastructural study." Pro Finn Dent Soc vol. 87, No. 4 (1991).
Giambro, N.J. et al "Characterization of Fluorosed Human Enamel by Color Reflectance, Ultrastructure, and Elemental Composition." Caries Res. Issue 29 (1995) pp. 251-257.
Reynolds, E.C. Remineralization of Enamel Subsurface Lesions by Casein Phosphopeptide-stabilized Calcium Phosphate Solutions. J Dent Res. vol. 76, Iss. 9, Sep. 1997. pp. 1587-1595.
Reynolds Eric C., Anticariogenic complexes of amorphous calsium phosphate stabilized by casein phosphopeptides: A review. Journal of Special Care in Dentistry vol. 18, No. 1 Jan./Feb. 1998 pp. 8-16.
Reynolds, E.C. et al. "Retention in Plaque and Remineralization of Enamel Lesions by Various Forms of Calcium in a Mouthrinse of Sugar-free Chewing Gum." J Des Res vol. 82 No. 3 (2003) pp. 206-211.
Shen P. et al, "Remineralization of Enamel Subsurface Lesions by Sugar-free Chewing Gum Containing Casein Phosphopeptide-Amorphous Calcium Phosphate." J Dent Res vol. 80 No. 12 (2001) pp. 2066-2070.
Fejerskov, O. et al "Dental fluorosis—a handbook for health workers." Copyright 1988 Munksgaard, Copenhagen.
Fejerskov, Ole et al. "Fluoride in Dentistry $2^{nd}$ edition." Copyright 1996 Munksgaard, Copenhagen.
Walker, Glen et al. "Increased remineralization of tooth enamel by milk containing added casein phosphopeptide-amorphous calcium phosphate." Journal of Dairy Research (2006) pp. 74-78.
Inaba, D et al. "Effect of Sodium Hypochlorite Treatment on Remineralization of Human Root Dentine in vitro." Caries Research 1996, vol. 30 pp. 218-224.
Adamson et al., "Characterisation of Tryptic Casein Phosphopeptides Prepared Under Industrially-Relevant Conditions", Biotec. Bioeng. (1995), 45, pp. 196-4.
Adamson et al., "High Performance Capillary Electrophoresis of Casein Phosphopeptides Containing 2-5 Phosphoseryl Residues; Relationship Between Absolute Electrophoretic Mobility and Peptide Charge and Size", Electrophoresis 16: pp. 525-528 (1995).

(Continued)

*Primary Examiner* — Walter Webb
(74) *Attorney, Agent, or Firm* — Merchant & Gould P.C.

(57) ABSTRACT

A method is provided for mineralizing a dental surface or subsurface including contacting the dental surface with a protein disrupting agent and stabilized amorphous calcium phosphate (ACP) or amorphous calcium fluoride phosphate (ACFP).

12 Claims, No Drawings

(56) References Cited

OTHER PUBLICATIONS

Adamson et al., "The Analysis of Multiple Phosphoseryl-Containing Casein Peptides Using Capillary Zone Electrophoresis", J. Chromatogr. (Sep. 3, 1993), 646:2, pp. 391-396.
Bavetta et al., "Protein Factors and Experimental Rat Caries", Nutr. 63: pp. 107-117 (1957).
Biesbrock, A.R. et al. "Reversal of Incipient and Radiographic Caries Through the Use of Sodium and Stannous Fluoride Dentifrices in a Clinical Trial." The Journal of Clinical Dentistry vol. IX, No. 1.
Biesbrock, Aaron R. "Relative anti-caries efficacy of 1100, 1700, 2200, and 2800 ppm fluoride ion in a sodium fluoride dentifrice over 1 year." Community Dentistry and Oral Epidemiology 2001;29: pp. 382-389.
Biesbrock, Aaron R. et al. "Dose response efficacy of sodium fluoride dentifrice at 9 and 21 months with supervised brushing."American Journal of Dentistry, vol. 16, No. 5, Oct. 2003.
Cai et al., "Remineralization of Enamel Subsurface Lesions in Situ by Sugar-Free Lozenges Containing Casein Phosphopeptide-Amorphous Calcium Phosphate", Aus. Dent. J. (2003) 48: 4, pp. 240-243.
CAPLUS Copyright 2005. NMR studies of a novel calcium, phosphate and fluoride delivery vehicle.
Cross et al., "NMR Studies of a Novel Calcium, Phosphate and Fluoride Delivery Vehicle—The Multiphosphorylated Peptide Alpha S1-Casein (589-79) Complexed with Amorphous Calcium Fluoride Phosphate", Biomaterials. Accepted for publication, Jan. 2004.
Cross et al., "Cation-Dependent Structural Features of Beta-Casein-(1-25)", Biochem. J. (May 15, 2001), 356: Pt 1, pp. 277-286.
Cross et al., "Structural Studies of the β-Casein Phosphopeptide Bound to Amorphous Calcium Phosphate", IADR, General Session, Chiba, Abstract 0490, (2001).
Cross et al., "Ultrastructural Studies of the Casein Phosphopeptide-Amorphous Calcium Phosphate Nanoclusters", IADR, General Session, Chiba, Abstract 0491, (2001).
Cross, Keith et al. Physicochemical Characterization . . . J. Biol. Chem. 2005, vol. 28, No. 16. 15362-15369.
Curnow M.M.T., et al. "A Randomised Controlled Trial of the Efficacy of Supervised Toothbrushing in High-Caries-Risk Children." Carie Research 2002; 36:294-300.
Database WPI Week 200316, Thomason Scientific, London, GB; 2003-165149, XP002537968 & SE 0 100 558 A, Mediteam Dental AB, Aug. 21, 2002. Abstract.
Davies G.M., "A randomized controlled trial of the effectiveness of providing free fluoride toothpaste from the age of 12 months on reducing caries in 5-6 year old children." Community Dental Health (2002) 19, 131-136.
Deangelis et al., "Molecular of Anticariogenic Casein Phosphopeptide AS2-CN (2-20) NMR Spectroscopy Derived Constraints", Abstract 2997-82$^{nd}$ General Session of the IADR, 2004, Honolulu, Hawaii.
Duckworth, R.M. "Oral Fluoride Measurements for Estimation of the Anti-caries Efficacy of Fluoride Treatments." J Dent Res. Apr. 1992.
Duckworth, R.M. "Effects of Mouthwashes of Variable NaF Concentration but Constant NaF Content on Oral Fluoride Retention." Caries Research 1994; 18:43-47.
Giniger et al. "A 180-Day Clinical Investigation of the Tooth Whitening Efficacy of a bleaching Gel with Added Amorphous Calcium Phosphate." J. of Clinical Dentistry. vol. XVI. No. 1. 2005. pp. 11-16.
Giniger et al. "The clinical performance of professionally dispensed bleaching gel with added amorphous calcium phosphate." *JADA*. vol. 136. 2005. pp. 383-392.
Harper et al., "Cariostatic Evaluation of Cheeses with Diverse Physical and Compositional Characteristics", Caries Res. 20: pp. 123-130 (1986).
Harper et al., "Modification of Food Cariogenicity in Rats by Mineral-Rich Concentrates from Milk", J. Dent Res. 66: pp. 42-45 (1987).
Hay et al., "A Clinical Trial of the Anticaries Efficacy of Casein Derivatives Complexed with Calcium Phosphate in Patients with Salivary Gland Dysfunction", Oral. Surg. Oral Med Oral. Pathol Oral Radiol. Endod. (2002); 93: pp. 271-275.

Hicks, John et al. "Biological factors in dental caries: role of remineralization and fluoride in the dynamic process of demineralization and remineralization (part 3)." The Journal of Clinical Pediatric Dentistry. vol. 28, No. 3 (2004).
Holloway et al., "Effects of Various Sucrose-Casein Ratios in Purified Diets on the Teeth and Supporting Structures of Rats", Arch Oral Biol. 3: pp. 185-200 (1961).
Holt et al., "Ability of a β-casein Phosphopeptide to modulate the precipitation of calcium phosphate by forming amorphous dicalcium phosphate nanoclusters." Biochem. J. (1996) 314, 1035-1039.
Holt et al. "Ability of a β-casein phosphopeptide to modulate the precipitation of calcium phosphate by forming amorphous dicalcium phosphate nanoclusters." *Biochem. J.* vol. 314. 1996. pp. 1035-1039.
Holt, Carl. "An equilibrium thermodynamic." Euro. Biophysics J. (2004) pp. 421-434.
Huq et al. "A H-NMR study of the casein Phosphopeptide $\alpha_{s1}$-casein(59-79)," Biochimica et biophysica Acta 1247 (1995) 201-208.
Huq et al., "Molecular Modelling of the Multiphosphorylated Casein Phosphopeptide Alpha S1-Casein (59-79) based on NMR constraints," J. Dairy Res. 71:1-5 (2004).
Huq et al., "Molecular Modeling of the Multiphosphorylated Sequence Motif Bound to Hydroxyapatite Surfaces" (59-79), J. Mol. Mode (2000), 6:35-47.
Huq, N. Laila et al. "Nascent Helix." J. of Peptide Science, (2003) pp. 386-392.
Iijima et al., "Acid Resistance of Enamel Subsurface Lesions Remineralized by a Sugar-Free Chewing Gum Containing Casein Phosphopeptide-Amorphous Calcium Phosphate (CPP-ACP)", Caries, Res. 2004; 38: pp. 551-556.
Kariya et al., "Fluoride Effect on Acid Resistance Capacity of CPP-ACP Containing Material", Abstract 2045—82$^{nd}$ General Session of the IADR, (2004), Honolulu, Hawaii.
Krobicka et al., "The Effects of Cheese Snacks on Caries in Desalivated Rats", J. Dent Res. 66:1116-19, (1987).
Larsson, K. Skold, et al. "Fluoride concentration in plaque in adolescents after topical application of different fluoride varnishes." Clin Oral Invest. (2000) 4:31-34.
Little, Elaine et al. "An equilibrium thermodynamic." Euro Biophysics J. vol. 33. pp. 435-447 (2004).
Lynch, R.J.M. et al, "Low-Levels of Fluoride in plaque and saliva and their effect on the demineralization and remineralisation of enamel; role of fluoride of toothpastes." International Dental Journal (2004) vol. 54/ No. 5.
Mazzaoui et al.,"Incorporation of Casein Phosphopeptide-Amorphous Calcium Phosphate into a Glass-ionomer Cement," J Dent Res 82(11):914-918, 2003.
Minami et al., "Effects of Cheese and Milk Containing CPP-ACP on Enamel Remineralization", 2049—82$^{nd}$ General Session of the IADR, 2004, Honolulu, Hawaii. Abstract only.
Murata M., "Remineralization Power by Xylitol Chewing Gums", Abstract 2046—82$^{nd}$ General Session of the IADR, 2004, Honolulu, Hawaii. Abstract only.
Perich et al., "Efficient Solution-Phase Synthesis of Multiple O-Phosphoseryl-Containing Peptides Related to Casein and Statherin", Int. J. Pept. Protein Res. (Aug. 1992), 40:2 pp. 81-88.
Perich et al., "The Use of Synthetic Phosphopeptides for Epitope Mapping of the AS1-Casein Phosphopeptide Segment 59-70", Bioorg. Med. Chem. Lett. (1992), 2: pp. 1153-1154.
Poitevin et al., "Clinical Effectiveness of a CPP-ACP Crème for Tooth Hypersensitivity Treatment", EADR Istanbul, (Aug. 24-28, 2004), Abstract 0136.
Ramalingam et al., "An in Vitro Investigation of the Effects of Casein Phosphopeptide-Stabilized Amorphous Calcium Phosphate (CPP-ACP) on Erosion of Human Dental Enamel by a Sports Drink", IADR, General Session, San Diego (2002), Abstract 2810.
Ramalingam et al., "Erosion of Human Dental Enamel by Sports Drinks", Synopses 27:16-19, (2003).
Reeves, "Calcium Phosphate Sequestering Phosphopeptide from Casein", Latour NG. Science 128: p. 472 (1958).
Reynolds et al., "A Review of the Effect of Milk on Dental Caries", Aust. J. Dairy Tech., 34, pp. 175-179 (1979).

(56) References Cited

OTHER PUBLICATIONS

Reynolds et al., "A Selective Precipitation Purification Procedure for Multiple Phosphoseryl-Containing Peptides and Methods for Their Identification", Anal. Biochem., (Mar. 1994), 217:2, pp. 277-284.
Reynolds et al., "Advances in Enamel Remineralization: Anticariogenic Casein Phosphopeptide-Amorphous Calcium Phosphate", J. Clin. Dent. (1999), X(2): pp. 86-88.
Reynolds et al., "Anticariogenicity of Calcium Phosphate Complexes of Tryptic Casein Phosphopeptides in the Rat", J. Dent. Res. (Jun. 1995), 74:6, pp. 1272-1279.
Reynolds et al., "Cariogenicity of a Confection Supplemented with Sodium Caseinate at a Palatable Level", Caries Res. 23: pp. 368-370 (1989).
Reynolds et al., "Confectionery Composition and Rat Caries", Caries Res. (1987) 21:6, pp. 538-545.
Reynolds et al., "Effect of Adsorbed Protein on Hydroxyapatite Zeta Potential and *Streptococcus mutans* Adherence", Infect. Immun. (Mar. 1983), 39:3, pp. 1285-1290.
Reynolds et al., "Effect of Casein and Whey-Protein Solutions on Caries Experience and Feeding Patterns of the Rat", Arch Oral Biol. (1984) 29:11 pp. 927-933.
Reynolds et al., "Effect of Milk on Caries Incidence and Bacterial Composition of Dental Plaque in the Rat", Arch Oral Biol. (1981) 26:5 pp. 445-451.
Reynolds et al., "Enamel Remineralization by Chewing Gum Containing Casein Phosphopeptide-Amorphous Calcium Phosphate", IADR, General Session, Chiba, Abstract 0489, (2001).
Reynolds et al., "Phosphoprotein Inhibition of Hydroxyapatite Dissolution", Calcif. Tissue Int. (1982), 34 Suppl. 2: S52-6.
Reynolds et al., "Protein Dissimilation by Human Salivary-Sediment Bacteria", J. Dent. Res. 68: pp. 124-129 (1989).
Reynolds et al., "Reduction of Chocolate's Cariogenicity by Supplementation with Sodium Caseinate", Caries Res. (1987), 21:5, pp. 445-451.
Reynolds, "Anticariogenic Casein Phosphopeptides", Prot. Peptide Lett. (1999), pp. 295-303.
Reynolds, "Caries Prevention and Oral Health", Health Aspects of Dairy Products/Caries Prevention and Oral Health, 2002. pp. 1306-1313.
Reynolds, "Dairy Components in Oral Health", Aust. J. Dairy Tech. 58: pp. 79-81, (2003).
Reynolds, "The Prevention of Sub-Surface Demineralization of Bovine Enamel and Change in Plaque Composition by Casein in an Intra-Oral Model", J. Dent. Res. (Jun. 1987) 66:6 pp. 1120-1127.
Reynolds, "The Role of Phosphopeptides in Caries Prevention", Dental Perspectives (1999), 3, pp. 6-7.
Roberts, "Role of Models in Assessing New Agents for Caries Prevention—Non-Fluoride Systems", Adv. Dent. Res. (Nov. 1995), 9(3), pp. 304-311; discussion 312-4.
Rose, "Binding Characteristics of *Streptococcus mutans* for Calcium and Casein Phosphopeptide", Caries. Res. (2000), 34, pp. 427-431.
Rose, "Effects of an Anticariogenic Casein Phosphopeptide on Calcium Diffusion in *Streptococcal* Model Dental Plaques", Arch Oral Biol. vol. 45, Issue 7, (2000) pp. 569-575.
Rosen et al., "Effect of Cheese, With and Without Sucrose, on Dental Caries and Recovery of *Streptococcus mutans* in Rats", J. Dent. Res. 633: pp. 894-896, (1984).
Sato et al. Sato et al. "Caries prevention Potential of a Tooth-coating Material Containing Casein Phosphopeptide-Amorphous Calcium Phosphate (CPP-ACP)," IADR, General session, Goteborg, 2003, Abstract 1007.
Schüpbach et al., "Incorporation of Caseinoglycomacropeptide and Caseinophosphopeptide into the Salivary Pellicle Inhibits Adherence of Mutans Streptococci", J. Dent. Res, vol. 75, pp. 1779-1788, (1996).
Silva, Margarita et al. "Fluoride content of infant formulae in Australia." Australian Dental Journal 1996:41:1.
Silva et al., "Effects of Water-soluble Components of Cheese on Experimental Caries in Humans," J Dent Res 66(1):38-41, Jan. 1987.

Talbo et al., "MALDI-PSD-MS Analysis of the Phosphorylation Sites of Caseinomacropeptide", Petides (Jul. 2001) 22:7, pp. 1093-1098.
Ten Cate, Jacob M. "Current concepts on the theories of the mechanism of action of fluoride."ACTA ODONTOL, SCAND 57 (1999).
White, "Use of Synthetic Polymer Gels for Artificial Carious Lesion Preparation" Caries Research 21, 1987, pp. 228-242. Abstract Only.
Zhao et al. "The remineralization for enamel lesions by casin phosphopeptide-amorphous calcium fluoride phospate in vitro." Zhonghua Kou Qiang Yi Kxue Za Zhi. vol. 36. No. 6. 2001. pp. 421-423.
Cross et al. "Casein Phosphopeptide-Amorphous Calcium Phosphate Nanocomplexes: A Model of the Casini Micelle Core," Centre for Oral Health Science, School of Dental Science, The University of Melbourne, pp. 1-42, Aug. 2008.
Hartshone, JE. "The relationship between plaque index scores, fluoride content of plaque, plaque pH, dental caries experience and fluoride concentration in drinking water in a group of primary school children." Journal of the Dental Association of South Africa, 49, pp. 5-10, 1994.
Reynolds et al. "Additional Aids to the Remineralisation of Tooth Structure," *Preservation and Restoration of Tooth Structure*, Chapter 8, Knowledge Books & Software, 111-118, 2005.
Translation of Russian Office Action from Application No. 2007123603, May 26, 2009.
Robinson et al., "Effect of Surface Zone Deproteinisation on the Access of Mineral Ions into Subsurface Carious Lesions of Human Enamel," *Caries Res* 1990; 24:226-230.
Schweigert BS et al. "Dental caries in the cotton rat. VI. The effect of the amount of protein, fat and carbohydrate in the diet on the incidence and extent of carious lesions". J.Nutr., vol. 31, 1946, pp. 439-447.
Shaw JH "Effects of dietary composition on tooth decay in the albino rat." J.Nutr. 41, 1950, pp. 23-23.
Loesche WJ "Role of *Streptococcus mutans* in human dental decay." Microbiol. Rev. vol. 50(4), Dec. 1950, pp. 353-380.
Kandelman D et al. "A 24-month clinical study of the incidence and progression of dental caries in relation to consumption of chewing gum containing xylitol in school preventive programs." J Dent Res vol. 69(11), 1990, pp. 1771-1775.
Featherstone JDB et al. "An in situ model for simultaneous assessment of inhibition of demineralization and enhancement of remineralization." J Dent Res vol. 71(Spec. Iss.), 1992, pp. 804-810.
Zero DT "In situ caries models." Adv Dent Res vol. 9(3), 1995, pp. 214-230.
Reynolds EC "Dairy products and dental health." Proceedings of the Nutrition Society of Australia, vol. 19, 1995, pp. 95-102.
Legeros RZ "Calcium phosphates in demineralization/remineralization processes." J Clinical Dent X, 1999, pp. 65-73.
Roberts MJ et al. "Remineralization of fluorotic enamel lesions by casein phosphopeptide—amorphous calcium fluorophosphate (CPP-ACFP) solution." IADR,ANZ division, Abstract 54, 2000.
Zhang L, et al. "Experimental study of phosphopeptide in promoting tooth remineralisation." J Dent Res., vol. 3(1), May 2000, pp. 27-30.
Reynolds EC "Health aspects of dairy products—Dairy products in relation to caries prevention and oral health." Invited review. Encycl Dairy Sciences, 2001.
Reynolds EC. "Remineralization of early enamel caries by anticariogenic casein phosphopeptide-amorphous calcium phosphate nanocomplexes." Dental Practice Nov./Dec. 2001.
Takamizawa T et al. "Determination of demineralization of tooth substrate by use of an ultrasonic device." Japan J Conserv Dent Jun vol. 47 Spring Issue 24—Abstract B-4, 2004.
Cross, KJ et al. "Casein Phosphopeptides in Oral Health—Chemistry and Clinical Applications", Current Pharmaceutical Design, vol. 13, 2007, pp. 793-800.
Allais, G. "Karies—Die Therapies." Continuing Dental Education, Jun. 2007, pp. 716-735. English Abstract.
Reich, E. "Flüssiger Zahnschmelz." Dental Magazine. 2005. English Abstract.
"GC Tooth Mousse—Eine ganz andere Art der Prävention." Dental Spiegel, Feb. 2005, pp. 53-54. English Abstract.

(56) References Cited

OTHER PUBLICATIONS

"GC stellt Kasein-haltige Zahnschutzcreme vor—Vorbeugen statt reparieren" DZW Special IDS-Nachlese. 2005. English Abstract.

"Tradition und modernes know how—ein Erfolgsrezept.", Zahn Prax 8, vol. 5, 2005, pp. 267. English Abstract.

"Minimale Intervention für maximale Mundgesundheit.", DZW Special. Mar. 2005. English Abstract.

Reich, E. "Das kleine gewisse Etwas zur Remineralisation", Zahnmedizin, vol. 95, No. 21, 2005. English Abstract.

Weiss, Dr. V. "Kariesprophylaxe in der kinderzahnnärztlichen Praxis", ZWP, Oct. 2005, pp. 76-79. English Abstract.

Chelariu, C. et al. "Nuove prospettive nella prevenzione della carieCongresso Nazionale del Collegio dei Docenti di Odontoiatria Roma", Apr. 5-7, 2006, Poster session, published by "Doctor Os", No. 3, Mar. 2006. English Abstract.

Reich, E. "GC Tooth Mousse—Ein neuer Ansatz zur Remineralisation", Kongress: Wissenschaft und Praxis der Sanften Zahnheilkunde, Lindau am Bodensee, Mar. 3-4, 2006. English Abstract.

Reynolds, EC et al. "Fluoride and casein phosphopeptide-amorphous calcium phosphate.", J Dent Res vol. 87, No. 4, 2008, pp. 344-348.

Piekarz, C. et al. "An in vitro assessment of the role of Tooth Mousse in preventing wine erosion.", Australian Dental Journal, vol. 53, 2008, pp. 22-25.

Kumar, VLN et al. "The effect of casein phosphopeptide-amorphous calcium phosphate on remineralization of artificial caries-like lesions: an in vitro study.", Australian Dental Journal, vol. 53, 2008, pp. 34-40.

Walsh, L. "Application of the System for Total Environmental Management(STEM) to demineralization, dental erosion and tooth wear.", Australasian Dental Practice, Jan.-Feb. 2008, pp. 52-58.

Rahiotis, C. et al. "Characterization of oral films formed in the presence of a CPP-ACP agent: An in situ study.", Journal of dentistry, vol. 36, 2008, pp. 272-280.

Wilfershausen, B. et al. "In-Vitro- Studie Zur Überprüfung einermöglichen Remeralisation durch caesinphosphopetidhaltige Calciumphosphat-komplexe (CPP_ACP).", Deutsche Zahnärztiche Zeitschrift, vol. 63, No. 2, 2008, pp. 134-139. English Abstract.

Morgan, MV et al. "The Anticariogenic Effect of Sugar-Free Gum Containing CPP-ACP Nanocomplexes on Approximal Caries Determined Using Digital Bitewing Radiography.", Caries Research, vol. 42, pp. 171-184, 2008.

Westerman, G. et al. "The Argon Laser and Remineralizing Paste with Fluoride Effects on Enamel Caries." AAPD,Washington, 2008.

Chalmers, J. et al. "Minimal Intervention Dentistry in the New Millennium.", DDS, MS. Dentaltown, Feb. 2008, pp. 54.

Morgan, MV et al. "A Clinical Trial Measuring White Spot Lesion Progression and Regression.", Abstract 0112, Jul. 2008, Toronto, Canada.

Cipolla, M. et al. "Fluoride and Calcium-Phosphate Effects on Fracture Toughness of Bleached Dentin.", Abstract 1032, Jul. 2008, Toronto, Canada.

Turssi, C.P. et al. "Progression of erosion following use of calcium and phosphorus compounds.", Abstract 2499, Jul. 2008, Toronto, Canada.

Ranjitkar, S. et al. "The role of tooth mousse in reducing erosive tooth wear.", Abstract 2500, Jul. 2008, Toronto, Canada.

Huang, A. et al. "Remineralization of eroded teeth using CPP-ACP paste.", Abstract 3267, Jul. 2008, Toronto, Canada.

Kim, K. et al. "Remineralization of the artificial caries lesion using CPP-ACP and fluoride.", Abstract 3280, Jul. 2008, Toronto, Canada.

Aytepe, Z. et al. "Effect of CCP-ACP on oral health of cerebral palsy children.", Abstract 3343, Jul. 2008, Toronto, Canada.

Theerapiboon, U. et al. "Remineralization of artificial caries by CPP-ACP paste.", Abstract 3274, Jul. 2008, Toronto, Canada.

Morgan, MV et al. "Clinical trial of tooth mousse on white spot lesions.", Cooperative research centre for oral health science. Toronto, Briefing paper No. 2, 2008.

Manton, D. et al. "Remineralization of enamel subsurface lesions in situ by the use of three commercially available sugar-free gums.", International Journal of Paediatric Dentistry, vol. 18, 2008, pp. 284-290.

Reynolds, E. "Calcium phosphate-based remineralization systems: scientific evidence?" Australian Dental Journal, vol. 53, 2008, pp. 268-273.

Quartarone, E. "Surface kinetic roughening caused by dental erosion: an atomic force microscopy study.", Journal of Applied physics, vol. 103, 2008, pp. 104702-1-104702-5.

Ferrazzano, G. Et al. "Protective effect of yogurt extract on dental enamel demineralization in vitro.", Australian Dental Journal, vol. 53, 2008, pp. 314-319.

Donovan, T. "Protocol for the prevention and management of root caries.", Journal Compilation, vol. 20, No. 6, 2008, pp. 405-411.

Manton, D. et al. "Effect of ozone and Tooth Mousse™ on the efficacy of peroxide bleaching.", Australian Dental Journal, vol. 53, 2008, pp. 128-132.

Manton, D. "Dental Caries: Where to From Here?", Ann Roy Austral Coll Dent Surg, vol. 19, 2008, pp. 73-76.

Gugnani, S. et al. "Comparative evaluation of two commercially available desensitising agents after scaling and root planning: an in vivo stud", PERIO, vol. 5, No. 2, 2008, pp. 121-129.

Gandolfi, M. et al. "Calcium silicate coating derived from Portland cement as treatment for hypersensitive dentine", Journal of Dentistry, vol. 36, 2008, pp. 565-578.

Pietrzycka, K. "Chemical methods of treatment of dental caries: the action and application of CPP-ACP.", E-Dentico, vol. 2, No. 18, 2008, pp. 68-74.

Carrillo, Dr. J et al. "Nuevos avances tecnológicos en Odontología Conservadora", La Gaceta Dental, vol. 193, Jun. 2008. English Abstract.

Reich, E. "Die Betreuung von Kariespatienten in der Praxis", Quintessenz, vol. 59, No. 12, 2008, pp. 1301-1307.

O'Hehir, T "Caries—More than a filling.", Hygientown.com, Jul./Aug. 2008, pp. 8-12.

Japanese Examination Report for corresponding Japanese Patent Application No. 2008-515000 mailed Mar. 7, 2013. English translation.

Reynolds EC "Dairy products and dental health." Proc Nutr Soc Aus vol. 76, 1997, pp. 1587-1595.

Shen, P. et al. "Enamel remineralization by a mouthrinse containing casein phosphopeptide-amorphous calcium phosphate and fluoride in an in situ model." Australian Dental Journal ADRF Special Research Supplement vol. 49, No. 4, 2004.

Ung, M. et al. "Investigation of the binding of casein phosphopeptides to the major enamel pellicle proteins.", Australian Dental Journal ADRF Special Research Supplement vol. 49, No. 4, 2004.

Lasfargues, J. et al. "La réminéralisation des lesions carieuses (2) synergies thérapautiques Realités Cliniques.", vol. 15, No. 3, 2004 pp. 261-275. English Abstract.

Miyazaki, M. et al. "Using ultrasound transmission velocity to analyze demineralization of tooth substrate." Abstract 94—$52^{nd}$ ORCA Congress, Jul. 2005, Indianapolis, USA / Caries Res vol. 39:319.

Holler, B. E. et al. "Fluoride uptake and distribution in enamel and dentin after application of different fluoride solutions." Clin Oral Invest, vol. 6, 2002, pp. 137-144.

Sakaguchi, Y. et al. "Preventing acid induced enamel demineralization using CPP-ACP containing paste." Abstract 2055—IADR, Mar. 2005, Baltimore, Maryland, USA.

Hicks, J. et al. "Casein Phosphopeptide-Amorphous calcium phosphate paste: root surface caries formation.", Abstract 3275—IADR, Mar. 2005, Baltimore, Maryland, USA.

Ferrazzano, G.F. et al. "Nuove strategie nella prevenzione della carie dentaria:studio sperimentale sui caseino-fosfopeptidi." Prevenzione Odontostomatologica vol. 4, 2005, pp. 15-21. English Abstract.

Chalmers, J.M. "Minimal intervention dentistry: part 1. Strategies for addressing the new caries challenge in older patients." JCDA, vol. 72, No. 5, 2006.

Manton, D.J. "Promoting remineralization: using casein phosphopeptide—stabilized amorphous calcium (fluoride) phosphate. A chemical approach." EAPD, Amsterdam Jun. 8-11, 2006.

(56) References Cited

OTHER PUBLICATIONS

Iijima, Y. et al. "Acid resistance of remineralized enamel by a sugar-free chewing gum.", Abstract 184—84th General Session of the IADR, Jun. 28-Jul. 1, 2006, Brisbane, Australia.

Manton, D. J. et al. "Remineralization of white spot lesions in situ by tooth mousse." Abstract 185—84th General Session of the IADR, Jun. 28-Jul. 1, 2006, Brisbane, Australia.

Shen, P. et al. "Remineralization by a mouthrinse containing CPP-ACP at pH 5.5.", Abstract 189—84th General Session of the IADR, Jun. 28-Jul. 1, 2006, Brisbane, Australia.

Cai, F. et al. "Remineralization by chewing gum containing CPP-ACP and citric acid." Abstract 190—84th General Session of the IADR, Jun. 28-Jul. 1, 2006, Brisbane, Australia.

Sakaguchi, Y. et al. "Remineralization potential of CPP-ACP and its synergy with fluoride.", Abstract 191—84th General Session of the IADR, Jun. 28-Jul. 1, 2006, Brisbane, Australia.

Cochrane, N.J. et al. "QLF and TMR analysis of CPP-ACFP remineralized enamel in vitro.", Abstract 192—84th General Session of the IADR, Jun. 28-Jul. 1, 2006, Brisbane, Australia.

Walsh, L.J. et al. "Effect of CPP-ACP versus potassium nitrate on cervical dentinal hypersensitivity.", Abstract 947—84th General Session of the IADR, Jun. 28-Jul. 1, 2006, Brisbane, Australia.

Wong, L, et al. "Plaque microcosm biofilm mineralization by CPP-ACP and calcium-phosphate-monofluorophosphate-urea mineralizing solution." Abstract 1269—84th General Session of the IADR, Jun. 28-Jul. 1, 2006, Brisbane, Australia.

Sukasaem, H. et al. "Effect of CPP-ACP on hardness of enamel eroded by Cola-drink." Abstract 1673—84th General Session of the IADR, Jun. 28-Jul. 1, 2006, Brisbane, Australia.

Narayana, T. et al. "An in vitro study of wear prevention in dentine." Abstract 2424—84th General Session of the IADR, Jun. 28-Jul. 1, 2006, Brisbane, Australia.

Ranjitkar, S. et al. Enamel wear prevention under conditions simulating bruxism and acid regurgitation. Abstract 2428—84th General Session of the IADR, Jun. 28-Jul. 1, 2006, Brisbane, Australia.

Morgan, M.V. et al. CPP-ACP gum slows progression and enhances regression of dental caries. Abstract 2445—84th General Session of the IADR, Jun. 28-Jul. 1, 2006, Brisbane, Australia.

Cross, K.J. et al. Structure and 15N-Dynamics of casein phosphopeptide-amorphous calcium phosphate nanocomplexes. Abstract 2534—84th General Session of the IADR, Jun. 28-Jul. 1, 2006, Brisbane, Australia.

Reynolds, E.C. et al. "Improved plaque uptake and enamel remineralization by fluoride with CPP-ACP." Abstract 2538—84th General Session of the IADR, Jun. 28-Jul. 1, 2006, Brisbane, Australia.

Sudjalim, T.R. et al. "Prevention of white spot lesions in orthodontic practice: a contemporary review.", Australian Dental Journal, vol. 51, No. 4, 2006, pp. 284-289.

Manton, D.J. et al. "In situ remineralisation by sugar-free gums, one containing CPP-ACP." Abstract 0020—45th Annual Meeting of Australian/New Zealand Division of the IADR, 2005, pp. 25-28.

Wong, R. et al. Incorporation of casein phosphopeptide-amorphous calcium phosphate into a temporary cement. Abstract 0653—84th General Session of the IADR, Jun. 28-Jul. 1, 2006, Brisbane, Australia.

Al-Zraikat, H. Et al. "Incorporation of casein-phosphopeptide-amorphous calcium phosphate into glass ionomer cement." Abstract 0654—84th General Session of the IADR, Jun. 28-Jul. 1, 2006, Brisbane, Australia.

Yamaguchi, K. et al. "Effect of CPP-ACP paste on mechanical properties of bovine enamel as determined by an ultrasonic device.", Journal of Dentistry vol. 34, 2006, pp. 230-236.

Yamaguchi, K. et al. "Ultrasonic determination of the effect of casein phosphopeptide-amorphous calcium phosphate paste on the demineralization of bovine dentin.", Caries Res, vol. 41, 2007, pp. 204-207.

Moule, C.A. et al. "Resin bonding using an all-etch or self-etch adhesive to enamel after carbamide peroxide and/or CPP-ACP treatment.", Australian Dental Journal, vol. 52, No. 2, 2007, pp. 133-137.

Oshiro, M. et al. "Effect of CPP-ACP paste on tooth mineralization: an FE-SEM study." Journal of oral Science, vol. 49, No. 2, 2007, pp. 115-120.

Rahiotis, C. et al. "Effect of a CPP-ACP agent on the demineralization and remineralization of dentine in vitro.", Journal of Dentistry, vol. 35, 2007, pp. 695-698.

Kariya, S. et al. "Remineralization of enamel lesion by a novel cream with both CPP-ACP and fluoride.", Poster session 136—54th Annual ORCA Congress, 2007.

Milnar, F.J. "Considering biomodification and remineralization techniques as adjuncts to vital tooth-bleaching regimens.", Compendium vol. 28, No. 5, 007, pp. 234-240.

Ng, H. et al. "Aesthetic management of severely fluorosed incisors in an adolescent female." Australian Dental Journal, vol. 52, No. 3, 2007, pp. 243-248.

Ardu, S. et al. "Minimally invasive treatment of white spot enamel lesions.", Quintessenz International, vol. 38, No. 8, 2007, pp. 633-636.

Rajnjitkar, S. et al. "The Role of Tooth Mousse in preventing enamel wear.", Poster 0375—session 39—42nd annual meeting of IADR-Continental European and Israeli Divisions, Sep. 26-29, 2007.

Tantbirojn, D. et al. "Changes in surface hardness of enamel by a cola drink and CPP-ACP paste.", Journal of Dentistry, vol. 36, 2008, pp. 74-79.

Keçik, D. et al. "Effect of Acidulated Phosphate Fluoride and Casein Phosphopeptide-Amorphous Calcium Phosphate Application on Shear Bond Strength of Orthodontic Brackets." Angle Orthodontist, vol. 78, No. 1, 2008, pp. 129-133.

Vlacic, J. et al. "Combined CPP-ACP and photoactivated disinfection (PAD) therapy in arresting root surface caries: a case report.", British Dental Journal, vol. 203, No. 8, 2007.

Misra, S. et al. "Early Childhood Caries—A Review.", Dental Update, vol. 34, 2007, pp. 556-564.

Mickenautsch, S. "An Introduction to Minimal Intervention Dentistry (MI).", Dental News, vol. XIV, No. IV, 2007.

Mount, GJ, "A new paradigm for operative dentistry.", Australian Dental Journal vol. 52, No. 4, 2007, pp. 264-270.

Rees, J. et al. "Pronamel and tooth mousse: An initial assessment of erosion prevention in vitro.", Journal of Dentistry, vol. 35, 2007, pp. 355-357.

Ferrazzano, G.F. et al. "New Strategies in dental caries prevention: experimental study on casein phosphopetide.", European Journal of Paedetric Dentistry, vol. 4, 2007.

Al-Zraikat, H. et al. "Development of GIC incorporating Caesin Phosphopetide amorphous phosphate (CPP_ACP) complex.", Australian Dental Journal ADRF Special Research Supplement, vol. 52, No. 4, 2007.

Cross, KJ et al. "Structural Characterization of Beta-casein(1-25)-ACFP Complex.", Aust Dent J ADRF Special Research Supplement, vol. 52, No. 4, 2007.

Cross, KJ et al. "Structural Characterization of anticariogenic casein Phosphopetide alphas2 casein(46-70) complexed with amorphous calcium phosphate.", Aust Dent J ADRF Special Research Supplement 200, vol. 52, No. 4, 2007.

Ramalingam, L. et al. "Adding Caesin Phosphopetide-amorphous Calcium Phosphate to Sports Drinks to Eliminate In Vitro Erosion.", Pediatric Dentistry, vol. 27, No. 1, 2005.

Trajtenberg, C.P. et al. "CPP-ACP Paste with Fluoride: In Vitro Root Surface Caries Formation.", Abstract 0500, IADR 2007 New Orleans, USA.

Westerman, G. et al. "Argon Laser and Remineralizing Paste Effect on Root Surface Caries.", Abstract 0018, IADR 2007, New Orleans, USA.

Fuller, B.L. et al. "Efficacy of MI Paste in Preventing Demineralization in Overdenture Abutments.", Abstract 0503, IADR 2007, New Orleans, USA.

Haderlie, D.D. et al. "MI Paste and Fluoride effects on Secondary Caries.", Abstract 0504, IADR 2007, New Orleans, USA.

Smolenski, D. et al. "1MI Paste and Fluoride for Caries Prevention In-Vitro.", Abstract 0505, IADR 2007, New Orleans, USA.

Xie, Q. et al. "Remineralization Effects of CPP-ACP and Proanthocyanidin on Artificial Root Caries.", Abstract 0512, IADR 2007, New Orleans, USA.

(56) References Cited

OTHER PUBLICATIONS

Smith, S. "Ultramorphological evaluation of dentin after treatment with different desensitizing agents.", Abstract 0941, IADR 2007, New Orleans, USA.
Freml, L. et al. "Efficacy of Hypersensitivity Agents on Demineralization under Provisional Crowns." Abstract 1346, IADR 2007, New Orleans, USA.
Burwell, A.K. et al. "Dentifrice Protection Against Dentin Demineralization in an In Vitro Study.", Abstract 1764, IADR 2007, New Orleans, USA.
Sheharyar, S. et al. "Efficacy of MI Paste for Sensitivity Associated With Vital Bleaching.", Abstract 2041, IADR 2007, New Orleans, USA.
Peschke, J.C. et al. "Nucleating Ability of Calcium Phosphate-Protein-Composites.", Abstract 2244, IADR 2007, New Orleans, USA.
Chen, L. et al. "Calcium Release and Mechanical Properties of Experimental Calcium-Releasing Composites.", Abstract 2572, IADR 2007, New Orleans, USA.
Wright, S. et al. "Artificial Caries Inhibited with MI Paste and Two Restorative Materials.", Abstract 2777, IADR 2007, New Orleans, USA.
Burwell, A.K. et al. "Quantitative Tubule Occlusion in an In Vitro Remineralization/Demineralization Model.", Abstract 0568, EADR 2006, Dublin, Ireland.
Ardu, S. et al. "A minimally invasive treatment of severe dental fluorosis.", Quintessence International, vol. 38, No. 6, 2007, pp. 455-458.
Cai, F. et al. "Effect of Addition of Citric Acid and Casein Phosphopeptide-Amorphous Calcium Phosphate to a Sugar-free chewing gum on Enamel Remineralization in Situ.", Caries Research, vol. 41, 2007, pp. 377-383.
Rini Sudjalim, T. et al. "Prevention of demineralization around orthodontic brackets in vitro.", American Journal of Orthodontics and Dentofacial Orthopedics, vol. 131, No. 6, 2007.
Sudjalim, T.R. et al. Prevention of demineralization around orthodontic brackets in vitro. . American Journal of Orthodontics and Dentofacial Orthopedics., 2007, pp. 705.e1-705. e9.
Allais, G. „Karies—Die Therapie., Continuing Dental Education, Jun. 2007, pp. 716-735.
Kowalczyk et al. "Evaluation of the product based on Recaldent™ technology in the treatment of dentin hypersensitivity.", Advances in Medical Sciences, vol. 51 suppl 1, 2006.
Pitts, N.B. "Are we ready to move from operative to non-operative/preventive treatment of dental caries in clinical practice?", Caries Res, vol. 38, 2004, pp. 294-304.
Adebayo, O.A. et al. "Effects of conditioners on microshear bond strength to enamel after carbamide peroxide bleaching and/or casein phosphopeptide-amorphous calcium phosphate (CPP-ACP) treatment", Journal of Dentistry, vol. 35, 2007, pp. 862-870.
Walshe, L.J. "The effects of GC Tooth Mousse on cervical dentinal sensitivity: a controlled clinical trial", International Dentistry SA—Australasian Edition vol. 5, No. 1, 2007.
William, V. et al. "Molar Incisor Hypomineralization: Review and Recommendations for Clinical Management", Pediatric Dentistry, vol. 28, No. 3, 2006.
Inaba, D. et al. "Intraoral changes in NaOCl-treated Root Dentin Lesions: A Pilot Study.", J. Dental Hlth, vol. 50, 2000, pp. 824-826.
Coates, L. "Tooth mousse shows some unexpected beneficial side effects." Dental Asia—Nov./Dec. 2004.
"Preventive agents." The Dental Advisor, vol. 21, No. 13, Dec. 2004.
Feinmann, J. "This won't hurt a bit.", The Times, Saturday, Mar. 12, 2005.
"Caséine phosphopeptide et phosphate de calcium amorphe: un complexe prometteur.", Dialogue dentaire, Printemps 2005 / N°30, pp. 27-29. English Abstract provided.
Minimum Intervention: modernes Kariesmanagement—Weg vom chirurgichen, hin zum medizinischen Versorgungsansatz mit GC. IDS—31st International Dental Show, Cologne, Apr. 12-16, 2005 (Today—Independent Trade Show Daily—Saturday).
Melkers, M.J. "Keeping focused on the finish line. Accomplishing goals with traditional and progressive technologies.", Dentaltown, vol. 5—Issue 11, 2004, pp. 60,62,64&66.
"Editors' Choice—Prospec MI Paste." The Dental Advisor, vol. 22, No. 5, Jun. 2005.
Lewis, J. "Brush, floss and mousse?" Women Dentistry Journal, Winter 2005, vol. 2, Issue 4.
"Tooth Mousse." Pierre qui roule n'amasse pas mousse? Ben si ! Clinic—Avril 2006—vol. 27, p. 218-219, English Abstract provided.
Rozwadowska, E. "Children and private dentistry." Private Dentistry, May 2006, pp. 109-113.
Reich, E. Dental Products Report Europe, Jan. 1, 2006.
Malcmacher, L. "Enamel Remineralization: The Medical Model of Practicing Dentistry.", Dentistry Today, Nov. 2006.
Malcmacher, L. "Vitamins for teeth.", Dental Economics, Oct. 2006.
Products for the dental hygienist—Desensitizers. The Dental Advisor, vol. 23, No. 6, Jul./Aug. 2006.
"Putting mouths where the money is.", DPRAsia, Jan./Feb. 2007.
Steinberg, S. "A modern paradigm for caries management, Part 1: Diagnosis and Treatment." Dentistry Today, Feb. 2007.
Steinberg, S. "A modern paradigm for caries management, Part 2: A practical protocol." Dentistry Today, Jun. 2007.
Stößer, L. "Kariesprotektive Eigenschaften des durch Caseinphosphopeptid stabilisierten amorphen Calciumphosphat-Nanokomplexes (CPP-ACP)",. Deutsche Zahnärztliche Zeitschrift, 62-2007-9, 2007.
Vladic, J. et al. "Combined CPP-ACP and photoactivated disinfection (PAD) therapy in arresting root surface caries: a case report.", British Dental Journal, vol. 203 No. 8, 2007.
Dr.Liz Coates. "Tooth Mousse shows some unexpected beneficial side effects", Dental Asia. Nov./Dec. 2004.
Dr.Yaso Ramadas, "The oral care for children with malignancies.", Synopses; The Newsletter of the Australian and New Zealand Society of Paediatric Dentistry, Issue 28, 2004.
Plate, U. et al. Investigation of the early mineralization on collagen in dentine of rat incisors by quantitative electron spectroscopic diffraction (ESD), Cell Tissue Res, vol. 278, 1994, pp. 543-547.
Khan, Dr. S. "White Spots on Teeth", Buzzle.com Intelligent Life on the Web, Jan. 2010.

\* cited by examiner

DENTAL MINERALIZATION

This application is a National Stage Application of PCT/AU2006/000785, filed 7 Jun. 2009, which claims benefit of Serial No. 2005902961, filed 7 Jun. 2005 in Australia and which applications are incorporated herein by reference. To the extent appropriate, a claim of priority is made to each of the above disclosed applications.

The present invention relates to a method of mineralizing a dental surface, in particular tooth enamel. Methods of mineralizing hypomineralized lesions (including subsurface lesions) in the tooth enamel caused by dental caries, dental erosion and fluorosis are also provided.

BACKGROUND

Common causes of hypomineralized lesions are caries and fluorosis.

Dental caries is initiated by the demineralization of hard tissue of the teeth usually by organic acids produced from fermentation of dietary sugar by dental plaque odontopathogenic bacteria. Dental caries is still a major public health problem. Further, restored tooth surfaces can be susceptible to further dental caries around the margins of the restoration. Even though the prevalence of dental caries has decreased through the use of fluoride in most developed countries, the disease remains a major public health problem. Dental erosion or corrosion is the loss of tooth mineral by dietary or regurgitated acids. Dental hypersensitivity is due to exposed dentinal tubules through loss of the protective mineralized layer, cementum. Dental calculus is the unwanted accretion of calcium phosphate minerals on the tooth surface. All these conditions, dental caries, dental erosion, dental hypersensitivity and dental calculus are therefore imbalances in the level of calcium phosphates.

Enamel fluorosis (mottling) has been recognized for nearly a century, however, the aetiological role of fluoride was not identified until 1942 (Black and McKay, 1916). The characteristic appearance of fluorosis may be differentiated from other enamel disturbances (Fejerskov et al., 1991). The clinical features of fluorotic lesions of enamel (FLE) represent a continuum ranging from fine opaque lines following the perikymata, to chalky, white enamel (Fejerskov et al., 1990; Giambro et al., 1995). The presence of a comparatively highly mineralized enamel outer surface and a hypomineralized sub-surface in the fluorotic lesion simulates the incipient enamel "white spot" carious lesion (Fejerskov et al., 1990). With increasing severity, both the depth of enamel involved in the lesion and the degree of hypomineralization increases (Fejerskov et al., 1990, Giambro et al., 1995). The development of fluorosis is highly dependent on the dose, duration and timing of fluoride exposure (Fejerskov et al., 1990, Fejerskov et al., 1996; Aoba and Fejerskov, 2002) and is believed to be related to elevated serum fluoride concentrations. Chalky "white spot" lesions may also form on developing teeth in children such as after treatment with antibiotics or fever. Such lesions indicate areas of hypomineralization of the tooth enamel.

Depending on lesion severity, fluorosis has been managed clinically by restorative replacement or micro-abrasion of the outer enamel (Den Besten and Thariani, 1992; Fejerskov et al., 1996). These treatments are unsatisfactory because they involve restorations or removal of tooth tissue. What is desired is a treatment that will mineralize the hypomineralized enamel to produce a natural appearance and structure.

Specific complexes of casein phosphopeptides and amorphous calcium phosphate ("CPP-ACP", available commercially as Recaldent™) have been shown to remineralize enamel subsurface lesions in vitro and in situ (Reynolds, 1998; Shen et al., 2001; Reynolds et al., 2003).

WO 98/40406 in the name of The University of Melbourne (the contents of which are herein incorporated fully by reference) describes casein phosphopeptide-amorphous calcium phosphate complexes (CPP-ACP) and CPP-stabilised amorphous calcium fluoride phosphate complexes (CPP-ACFP) which have been produced at alkaline pH. Such complexes have been shown to prevent enamel demineralization and promote remineralization of enamel subsurface lesions in animal and human in situ caries models (Reynolds, 1998).

The CPP which are active in forming the complexes do so whether or not they are part of a full-length casein protein. Examples of active (CPP) that can be isolated after tryptic digestion of full length casein have been specified in U.S. Pat. No. 5,015,628 and include peptides Bos $\alpha_{s1}$-casein X-5P (f59-79) [1], Bos β-casein X-4P (f1-25) [2], Bos $\alpha_{s2}$-casein X-4P (f46-70) [3] and Bos $\alpha_{s2}$-casein X-4P (f1-21) [4] as follows:

[1] Gln$^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-Lys$^{79}$ $\alpha_{s1}$(59-79)

[2] Arg$^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-Arg$^{25}$ β(1-25)

[3] Asn$^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-Lys$^{70}$ $\alpha_{s2}$(46-70)

[4] Lys$^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-Lys$^{21}$ $\alpha_{s2}$(1-21)

The access of mineralizing ions to the tooth enamel in many cases can be limited by the layer of salivary proteins that forms over the surface of the enamel, termed the pellicle. The proteins of the pellicle can also accumulate in sub-surface enamel lesions, thereby inhibiting the mineralization of these lesions. Such accumulations of proteins can discolour over time, leaving unsightly patches on the tooth. Accordingly, there is a need to remove these proteins to remove discolouration and avoid limitations of access to the enamel by remineralizing ions. To overcome these and other limitations of known treatments, research to this end has been conducted.

SUMMARY OF THE INVENTION

In one aspect, the present invention provides a method of mineralizing a dental surface or sub-surface including contacting the dental surface with a protein disrupting agent, and contacting the dental surface with stabilized amorphous calcium phosphate (ACP) or amorphous calcium fluoride phosphate (ACFP). The dental surface is preferably dental enamel. In one embodiment the dental surface is a lesion in the enamel, such as a lesion caused by caries, dental erosion or fluorosis.

Mineralization of dental surfaces can be significantly enhanced by the disruption of pellicle proteins from the dental surface prior to the application of a remineralizing material, such as stabilised ACP and/or ACFP. In particular, it has been found that the mineralization of enamel by stabilized soluble forms of ACP(CPP-ACP) and ACFP (CPP-ACFP) is enhanced by pre-treatment of the enamel surface with a protein disrupting agent such as alkaline bleach.

Preferably the ACP and/or ACFP is phosphopeptide (PP)-stabilized. Preferably, the phosphopeptide (as defined below) is a casein phosphopeptide.

In a preferred embodiment the ACP and/or ACFP is in the form of a casein phosphopeptide stabilized ACP and/or ACFP complex.

Preferably, the phase of the ACP is predominantly a basic phase, wherein the ACP comprises predominantly the species $Ca^{2+}$, $PO_4^{3-}$ and $OH^-$. The basic phase of ACP may have the general formula $[Ca_3(PO_4)_2]_x[Ca_2(PO_4)(OH)]$ where $x \geq 1$. Preferably $x=1-5$. More preferably, $x=1$. Preferably the two components of the formula are present in equal proportions. Accordingly, in one embodiment, the basic phase of ACP has the formula $Ca_3(PO_4)_2Ca_2(PO_4)(OH)$.

Preferably, the phase of the ACFP is predominantly a basic phase, wherein the ACFP comprises predominantly the species $Ca^{2+}$, $PO_4^{3-}$ and $F^-$. The basic phase of ACFP may have the general formula $[Ca_3(PO_4)_2]_x[Ca_2(PO_4)F]_y$ where $x \geq 1$ when $y=1$ or where $y \geq 1$ when $x=1$. Preferably, $y=1$ and $x=1-3$. More preferably, $y=1$ and $x=1$. Preferably the two components of the formula are present in equal proportions. Accordingly, in one embodiment, the basic phase of ACFP has the formula $Ca_3(PO_4)_2Ca_2(PO_4)F$.

In one embodiment, the ACP complex consists essentially of phosphopeptides, calcium, phosphate and hydroxide ions and water.

In one embodiment, the ACFP complex consists essentially of phosphopeptides, calcium, phosphate, fluoride and hydroxide ions and water.

DETAILED DESCRIPTION OF THE INVENTION

Any suitable protein disrupting agent can be used in the method of the present invention. The agent is required to reduce the proteinaceous barrier formed over the surface to be treated, such as the pellicle over teeth. Examples of suitable agents include bleach, detergent, chaotropic agents such as urea, high phosphate concentrations, cocktails of proteases (e.g. endopeptidases, proteinases and exopeptidases) and any other protein solubilizing, disrupting or hydrolysing agent. Examples of suitable bleaches include sodium hypochlorite (NaOCl), and cabamide peroxide bleaches. In a preferred embodiment, the bleach is an alkaline bleach. In a further preferred embodiment the alkaline bleach is NaOCl. The protein disrupting agent acts to solubilize and partially or wholly remove proteins from the dental surface, particularly proteins of the pellicle.

In a further aspect of the present invention there is provided a method of mineralizing a dental surface comprising providing a protein disrupting agent and a source of ACP or ACFP. In a preferred embodiment the dental surface is enamel.

In a further aspect of the present invention there is provided a method for treating fluorosis comprising contacting a fluorotic lesion in tooth enamel with a protein disrupting agent and stabilized ACP and/or ACFP.

In a further aspect of the present invention there is provided a method for treating dental caries comprising contacting a caries lesion in tooth enamel with a protein disrupting agent and stabilized ACP and/or ACFP.

In a further aspect of the present invention there is provided a method for treating dental erosion comprising contacting a lesion in tooth enamel caused by erosion with a protein disrupting agent and stabilized ACP and/or ACFP.

In a further aspect of the present invention there is provided a method for reducing white spot lesions on the tooth enamel comprising contacting a white spot lesion with a protein disrupting agent and stabilized ACP and/or ACFP.

In a further aspect of the present invention there is provided a method for remineralizing a lesion in tooth enamel comprising contacting the lesion with a protein disrupting agent and stabilized ACP and/or ACFP.

Preferably the ACP and/or ACFP is stabilized by a phosphopeptide. In a preferred embodiment the phosphopeptide is a casein phosphopeptides. Preferably, the ACP or ACFP is in the form of a casein phosphopeptide stabilized ACP or ACFP complex.

In one embodiment, the protein disrupting agent is NaOCl. A concentration of about 1 to 20% NaOCl may be used. Alternatively, the concentration of NaOCl is 1 to 10%. In a preferred embodiment, about 5% NaOCl is used.

The protein disrupting agent may be contacted with the dental surface for a period of about 1 to 60 minutes, or for about 1 to 30 minutes. In one embodiment, the protein disrupting agent is contacted with the dental surface for about 20 minutes.

Preferably the stabilized ACP and/or ACFP is contacted with the dental surface for a period of about 1 minute to 2 hours, or 5 minutes to 60 minutes or about 10 minutes. The stabilized ACP and/or ACFP may be repeatedly applied to the dental surface over a period of 1 day to several months.

In one embodiment, the stabilized ACP and/or ACFP is contacted with the dental surface after the dental surface has been contacted with the protein disrupting agent.

In a preferred embodiment, the protein disrupting agent is contacted with the dental surface 1 to 60 minutes, or 1 to 30 minutes, or 1 to 5 minutes prior to contacting the dental surface with the stabilized ACP and/or ACFP.

In a further aspect of the present invention there is provided a method for mineralizing a tooth surface comprising applying an ACP and/or ACFP complex to a tooth surface that has been pre-treated with a protein disrupting agent. Preferably the tooth surface is tooth enamel. In a preferred embodiment, the tooth surface is tooth enamel containing a lesion selected from the group consisting of one or more of a white spot lesion; a fluorotic lesion; a caries lesion; or a lesion caused by tooth erosion. In a further preferred embodiment the protein disrupting agent is a bleach.

In one embodiment, the dental surface is in need of such treatment. The invention also includes a method of treating a subject suffering fluorosis, dental caries, dentinal hypersensitivity or dental calculus.

Without being bound by any theory or mode of action it is understood that pre-conditioning tooth enamel with a protein disrupting agent results in partial or complete enamel de-proteination, enhancing the diffusion of calcium and phosphate into subsurface enamel.

It is further understood that treatment of tooth enamel with stabilised ACFP produces fluorapatite, which is more resistant to acid challenge than normal tooth enamel. This may result in tooth enamel with superior caries resistant properties. Accordingly, in a preferred embodiment the method of the present invention includes stabilised ACFP.

"Phosphopeptide" in the context of the description of this invention means an amino acid sequence in which at least one amino acid is phosphorylated. Preferably, the phosphopeptide includes one or more of the amino acid sequence -A-B-C-, where A is a phosphoamino residue, B is any amino acyl residue including a phosphoamino residue and C is selected from a glutamyl, aspartyl or phosphoamino residue. Any of the phosphoamino residues may independently be a phosphoseryl residue. B is desirably a residue the side-chain of which is neither relatively large nor hydrophobic. It may be Gly, Ala, Val, Met, Leu, Ile, Ser, Thr, Cys, Asp, Glu, Asn, Gln or Lys.

In another embodiment, at least two of the phosphoamino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are a phosphoamino acid. In a preferred embodiment, the phosphoamino acid residues are phosphoserine, most preferably three contiguous phosphoserine residues. It is also preferred that D and E are independently glutamic or aspartic acid.

It will also be understood that the term "comprises" (or its grammatical variants) as used in this specification is equivalent to the term "includes" and may be used interchangeably and should not be taken as excluding the presence of other elements or features.

In one embodiment, the ACP or ACFP is stabilized by a casein phosphopeptide (CPP), which is in the form of intact casein or fragment of the casein, and the complex formed preferably has the formula $[CPP(ACP)_8]_n$ or $[(CPP)(ACFP)_8]_n$ where n is equal to or greater than 1, for example 6. The complex formed may be a colloidal complex, where the core particles aggregate to form large (eg 100 nm) colloidal particles suspended in water. Thus, the PP can be a casein protein or a polyphosphopeptide.

The PP may be from any source; it may be present in the context of a larger polypeptide, including a full length casein polypeptide, or it may be isolated by tryptic or other enzymatic or chemical digestion of casein, or other phosphoamino acid rich proteins such as phosphitin, or by chemical or recombinant synthesis, provided that it comprises the sequence -A-B-C- or A-B-C-D-E as described above. The sequence flanking this core sequence may be any sequence. However, those flanking sequences in $\alpha_{s1}(59-79)$ [1], $\beta(1-25)$ [2], $\alpha_{s2}(46-70)$ [3] and $\alpha_{s2}(1-21)$ [4] are preferred. The flanking sequences may optionally be modified by deletion, addition or conservative substitution of one or more residues. The amino acid composition and sequence of the flanking region are not critical.

Examples of conservative substitutions are shown in Table 1 below.

TABLE 1

| Original Residue | Exemplary Conservative Substitution | Preferred Conservative Substitution |
|---|---|---|
| Ala | Val, Leu, Ile | Val |
| Asn | Gln Lys His Phe | Gln |
| Gln | Asn | Asn |
| Gly | Pro | Pro |
| Ile | Leu, Val, Met, Ala, Phe | Leu |
| Leu | Ile, Val, Met, Ala, Phe | Ile |
| Lys | Arg, Gln, Asn | Arg |
| Phe | Leu, Val, Ile, Ala | Leu |
| Pro | Gly | Gly |
| Ser | Thr | Thr |
| Val | Ile, Leu, Met, Phe, Ala | Leu |
| Asp | Glu | Glu |
| Thr | Ser | Ser |
| Trp | Tyr | Tyr |
| Tyr | Trp Phe Thr Ser | Phe |

The flanking sequences may also include non-naturally occurring amino acid residues. Commonly encountered amino acids which are not encoded by the genetic code, include:
2-amino adipic acid (Aad) for Glu and Asp;
2-aminopimelic acid (Apm) for Glu and Asp;
2-aminobutyric (Abu) acid for Met, Leu, and other aliphatic amino acids;
2-aminoheptanoic acid (Ahe) for Met, Leu and other aliphatic amino acids;
2-aminoisobutyric acid (Aib) for Gly;
cyclohexylalanine (Cha) for Val, and Leu and Ile;
homoarginine (Har) for Arg and Lys;
2,3-diaminopropionic acid (Dpr) for Lys, Arg and His;
N-ethylglycine (EtGly) for Gly, Pro, and Ala;
N-ethylasparigine (EtAsn) for Asn, and Gln;
Hydroxyllysine (Hyl) for Lys;
allohydroxyllysine (AHyl) for Lys;
3-(and 4) hydroxyproline (3Hyp, 4Hyp) for Pro, Ser, and Thr;
alloisoleucine (AIle) for Ile, Leu, and Val;
p-amidinophenylalanine for Ala;
N-methylglycine (MeGly, sarcosine) for Gly, Pro, Ala.
N-methylisoleucine (MeIle) for Ile;
Norvaline (Nva) for Met and other aliphatic amino acids;
Norleucine (Nle) for Met and other aliphatic amino acids;
Ornithine (Orn) for Lys, Arg and His;
Citrulline (Cit) and methionine sulfoxide (MSO) for Thr, Asn and Gln;
N-methylphenylalanine (MePhe), trimethylphenylalanine, halo (F, Cl, Br and I) phenylalanine, triflourylphenylalanine, for Phe.

In one embodiment, the PP is one or more phosphopeptides selected from the group consisting of $\alpha_{s1}(59-79)$ [1], $\beta(1-25)$ [2], $\alpha_{s2}(46-70)$ [3] and $\alpha_{s2}(1-21)$ [4].

In another embodiment of the invention, the stabilised ACFP or ACP complex is incorporated into oral compositions such as toothpaste, mouth washes or formulations for the mouth to aid in the prevention and/or treatment of dental caries, tooth decay, dental erosion or fluorosis. The ACFP or ACP complex may comprise 0.01-50% by weight of the composition, preferably 1.0-50%. For oral compositions, it is preferred that the amount of the CPP-ACP and/or CPP-ACFP administered is 0.01-50% by weight, preferably 1.0%-50% by weight of the composition. In a particularly preferred embodiment, the oral composition of the present invention contains about 2% CPP-ACP, CPP-ACFP or a mixture of both. The oral composition of this invention which contains the above-mentioned agents may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. The oral composition according to this invention may further include additional well known ingredients depending on the type and form of a particular oral composition.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 5 to about 9 and typically from about 5.0 to 7.0. The pH can be controlled with acid (e.g. phosphoric acid, citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In other desirable forms of this invention, the stabilised ACP or ACFP composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 $cm^2/g$., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a jar of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The invention also provides an ACP or ACFP composition as described above further including a protein disrupting agent. In one embodiment, the protein disrupting agent is a bleach. In a preferred embodiment the bleach is NaOCl.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

In a further aspect, the invention provides compositions including pharmaceutical compositions comprising any of the ACFP and/or ACP complexes as described above together with a protein disrupting agent and a pharmaceutically-acceptable carrier. Such compositions may be selected from the group consisting of dental, anticariogenic compositions and therapeutic compositions. Dental compositions or therapeutic compositions may be in the form of a gel, liquid, solid, powder, cream or lozenge. Therapeutic compositions may also be in the form of tablets or capsules. In one embodiment, the ACP and/or ACFP complexes are substantially the only remineralizing active components of such a composition, For example, a crème formulation may be employed containing: water; glycerol; CPP-ACP; D-sorbitol; silicon dioxide; sodium carboxymethylcellulose (CMC-Na); propylene glycol; titanium dioxide; xylitol; phosphoric acid; guar gum; zinc oxide; sodium saccharin; ethyl p-hydroxybenzoate; magnesium oxide; butyl p-hydroxybenzoate and propyl p-hydroxybenzoate.

The invention further includes a formulation described above provided together with instructions for its use to treat or prevent any one or more of dental caries or tooth decay, dental erosion and fluorosis.

In one embodiment, the active components of the composition consist essentially of the protein disrupting agent and stabilised ACP and/or ACFP. It is believed, without being bound by any theory or mode of action, that the stabilised ACP and/or ACFP and the protein disrupting agent are central to the therapeutic or preventative effect of the above embodiments of the invention, and thus embodiments consisting essentially of those components (with carriers, excipients and the like as required) are included within the scope of the invention.

The invention also relates to a kit for the treatment or prevention of one or more of dental caries, fluorosis and dental erosion including (a) a protein disrupting agent and (b) a CPP-ACP or CPP-ACFP complex in a pharmaceutically acceptable carrier. Desirably, the kit further includes instructions for their use for the mineralization of a dental surface in a patent in need of such treatment. In one embodiment, the agent and the complex are present in suitable amounts for treatment of a patient.

In a further aspect, there is provided a method of treating or preventing one or more of each of dental caries, tooth decay, dental erosion and fluorosis, comprising the steps of administering a protein disrupting agent to the teeth of a subject followed by administering an ACP or ACFP complex or composition. Topical administration of the complex is preferred. The method preferably includes the administration of the complex in a formulation as described above.

In a further aspect there is provided the use of a protein disrupting agent in the manufacture of a first composition and use of stabilized amorphous calcium phosphate (ACP) or amorphous calcium fluoride phosphate (ACFP) in a manufacture of a second composition, the first and second compositions being used for the treatment and/or prevention of one or more of dental caries, tooth decay, dental erosion and fluorosis, wherein the first composition is applied to a dental surface prior to the second composition.

In a further aspect there is provided a first composition including a protein disrupting agent and a second composition including stabilized amorphous calcium phosphate (ACP) or amorphous calcium fluoride phosphate (ACFP) for the treatment and/or prevention of one or more of dental caries, tooth decay, dental erosion and fluorosis, wherein the first composition is applied to a dental surface prior to the second composition.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

The invention will now be further described with reference to the following non-limiting examples.

One example of a mineralizing composition is a composition comprising the following (in decreasing order of proportion):
water
glycerol
CPP-ACP
D-sorbitol
silicon dioxide
sodium carboxymethylcellulose (CMC-Na)
propylene glycol
titanium dioxide
xylitol
phosphoric acid
guar gum
zinc oxide
sodium saccharin
ethyl p-hydroxybenzoate
magnesium oxide
butyl p-hydroxybenzoate
propyl p-hydroxybenzoate Such a composition is available from GC corporation under the name Tooth Mousse™. This is suitable for use after a protein disrupting agent, and is in the form of a paste or crème to facilitate its retention on teeth for a suitable period. Alternatively, this mineralizing composition may contain a protein disrupting agent, such as sodium hypochlorite.

The effectiveness of the invention may be demonstrated as follows.

Seven premolar teeth with FLE (Thylstrup Fejerskov Index, TF=3) were selected from teeth extracted for orthodontic reasons from healthy patients aged 10-28 years from the Royal Dental Hospital of Melbourne, Australia. Informed patient consent was obtained for the extracted teeth and the study protocol was approved by the Human Research Ethics Committee of The University of Melbourne. All specimens were debrided of adherent soft tissue and stored in 18% w/v formalin acetate solution at room temperature.

The teeth were cleaned with a rotating rubber cup and pumice and rinsed in double de-ionized water (DDW) (Fejerskov et al., 1988). The anatomical crowns were sectioned from the roots using a water-cooled diamond blade. Each crown was sectioned to provide a pair of enamel blocks each containing a FLE. A 4×4 mm² window was created over each lesion by placing a rectangular piece of Parafilm® (American National Can, Chicago, Ill., USA.) over the lesion and covering the surrounding enamel with nail varnish (Revlon™, New York, USA). The parafilm was then carefully removed to reveal the enamel lesion window which was divided into halves as control and test windows. The control window was covered with nail varnish. The two lesions of each specimen were randomly assigned to one of two remineralization groups; Group I—treatment with 5% w/v CPP-ACFP and Group II—treatment with 5% w/v CPP-ACFP immediately following pre-conditioning with 5.25% NaOCl.

CPP-ACFP was obtained from Recaldent Pty Ltd (Melbourne, Australia) and contained 47.6% w/w CPP, 15.7% w/w $Ca^{2+}$, 22.9% w/w $PO_4^{3-}$ and 1.2% w/w $F^-$. The CPP-ACFP was dissolved in distilled and deionized water at 5% w/v and adjusted to pH 7.0 with HCl. For the first group, each specimen was placed in 2 ml of 5% w/v, CPP-ACFP in a 5 ml plastic vial at 37° C. The CPP-ACFP solution was changed daily for 10 days. For the second group, each specimen was placed in a 5.25% NaOCl solution for 20 mins, rinsed and then placed in 2 ml of 5% w/v CPP-ACFP in a 5 ml plastic vial at 37° C. The CPP-ACFP solution was changed daily for 10 days.

A Chroma Meter (Minolta ChromaMeter CR241, Minolta, Japan) was used to record surface reflectance. Surface reflectance measurement was established in L*a*b* color space by the Commission de L'Eclairage in 1978, and measurements relate to human colour perception in three colour dimensions (Commision Internationale de L'Eclaige, 1978). The L* values represent colour gradients from white to black, a* values represent colour gradients from green to red, and b* values represent colour gradients from blue to yellow (Commision Internationale de L'Eclaige, 1978). Only L* value measurements were used in this study with whiter colours having a higher reading, and darker colours a lower reading. To ensure a reproducible position of specimens in the Chroma Meter, a wax mold for each sample was prepared and stored. All samples were air-dried with a dental triplex syringe for 60 s before each measurement. Individual specimens were repositioned ten times both before and after treatment, and colour reflectance L* values were recorded.

Each specimen was removed from the mineralizing solution and rinsed in DDW for 60 s and blotted dry with blotting paper. The nail varnish on the control window was removed gently with acetone. The control and test windows were then separated by cutting through the midline between the windows. The two half-slabs were then placed with the lesion windows parallel and embedded in cold curing methacrylate resin (Paladur, Heraus Kulzer, Germany). The two paired enamel half-slabs were then sectioned, and subjected to microradiography and microdensitometric image analysis to determine mineral content exactly as described by Shen et al. (2001).

An area free of defects close to the midline of each microradiographic image of each lesion (control and test) was chosen and scanned six times (Shen et al., 2001). Each scan comprised 200 readings, taken from the enamel surface to the mid-enamel region to include the total fluorotic lesion. The test (CPP-ACFP-treated) lesion was scanned to exactly the same depth as the control (untreated) lesion. The gray values obtained from each scan were converted to the equivalent thickness of aluminium (tA) using the image of the aluminium stepwedge included with each section (Shen et al., 2001). Using the formula of Angmar et al. (1963), the percentage volume of mineral was obtained for each reading as follows: V=(52.77(tA)−4.54)/tS. Where: V=volume of mineral as a percentage; tA=the relative thickness of aluminium obtained from the gray value scanned; and tS=section thickness (80 μm).

From the densitometric profile of [(vol % min versus lesion depth (mm)] for each lesion DZ values were calculated using trapezoidal integration (Reynolds, 1997). The difference between the area under the profile of the untreated fluorotic enamel in the control window with adjacent normal enamel was designated DZf, and the difference between the area under the CPP-ACFP-treated fluorotic enamel in the test window and adjacent normal enamel was designated DZr. Percentage mineralization (% M) of the fluorotic lesion was therefore (1−DZr/(DZf)×100 (Reynolds, 1997).

Following the microradiography the sections containing both control and mineralized FLE were subjected to Energy Dispersive X-ray Analysis (EDAX) as described previously (Reynolds, 1997).

Mean L* values were compared using a one way classification analysis of variance (ANOVA) with a Scheffe multiple comparison. The mean % M values were also compared using a one-way ANOVA. Overall mean L* and % M values were analysed using a paired data Student's t-test.

The L*values of the untreated fluorotic enamel lesions ranged from 79.1 to 87.8 with a mean value of 83.6±3.6

(Table 1). Treatment with 5% CPP-ACFP significantly reduced the L* value to 74.6±4.1, which was not significantly different to normal enamel (Table 1). Pre-conditioning with NaOCl followed by 5% CPP-ACFP treatment significantly reduced the L* value to 72.6±5.6, which was also not significantly different to normal enamel (Table 1). There was no significant difference in L* values for the two post-treatment (CPP-ACFP and NaOCl/CPP-ACFP) groups. The appearance of the surface enamel of both treatment groups had substantially improved with both exhibiting the appearance of normal, translucent enamel.

The difference between the mineral content of sound enamel and that of the pre-treatment lesions (DZf) varied from 426 to 12,048 vol % min. mm (Table 2). No correlation was found between surface reflectance (L*) and DZf of the untreated FLE. Treatment with 5% CPP-ACFP alone substantially increased the mineral content of the fluorotic lesions to restore 32.7% to 55.5% of the missing mineral, with a mean value of 44.8±10.6% (Table 2). Restoring 100% of the missing mineral would convert the entire lesion to sound enamel with respect to mineral content. Pre-conditioning of the enamel with NaOCl before CPP-ACFP treatment increased mineral uptake from 73.6% to 92.8% of the missing mineral with a mean value of 80.1±7.8% (Table 2). Energy dispersive X-ray analysis of the mineralized lesion of the transverse sections confirmed the mineral formed by the CPP-ACFP treatment was a fluoride-containing apatite.

In the clinic, as an example of a patient in need of remineralizing treatment of the tooth enamel, the patient is treated using the steps of:

1. Pretreating an enamel area in need of treatment, isolated using a rubber dam, with a 5% solution of NaOCl for 5 minutes.
2. Removing the NaOCl solution from the area with a moist cotton bud.
3. Applying the CPP-ACP-containing topical crème Tooth Mousse™ (GC Corporation) to the enamel surface immediately for 5 minutes and then the patient further applies the Tooth Mousse™ nightly without rinsing for four weeks.

It will be understood that the invention disclosed and defined in this specification extends to all alternative combinations of two or more of the individual features mentioned or evident from the text or drawings. All of these different combinations constitute various alternative aspects of the invention.

REFERENCES

Angmar B, Carlstrom D, Glas J E (1963). Studies on the ultrastructure of dental enamel. IV. The mineralization of normal human enamel. J Ultrastruct Res 8:12-23.
Aoba T, Fejerskov O (2002). Dental fluorosis: chemistry and biology. Crit. Rev Oral Biol Med 13:155-70.

TABLE 1

Effect of 5% CPP-ACFP with and without NaOCl pre-conditioning on colour reflectance (L*) of fluorotic enamel specimens

| Fluorotic enamel specimens | Colour Reflectance (L*) Values | | | | | | | |
|---|---|---|---|---|---|---|---|---|
| | I | II | III | IV | V | VI | VII | Overall Mean |
| Pre-treatment | 82.9 ± 0.9[a] | 85.5 ± 1.8 | 84.3 ± 0.4 | 82.5 ± 1.3 | 87.8 ± 0.6 | 79.1 ± 0.9 | 83.0 ± 0.6 | 83.6 ± 3.6 |
| Post-CPP-ACFP treatment | 74.1 ± 0.7[b] | 72.0 ± 0.5 | 78.2 ± 0.4 | 76.1 ± 0.7 | 79.5 ± 0.8 | 69.7 ± 1.5 | 72.3 ± 1.7 | 74.6 ± 4.1[c] |
| Post-NaOCl/CPP-ACFP treatment | 69.2 ± 1.0[b] | 72.3 ± 1.1 | 76.9 ± 1.4 | 72.2 ± 1.3 | 78.5 ± 1.4 | 61.6 ± 1.2 | 77.4 ± 1.0 | 72.6 ± 5.6[c] |

[a] n = 20
[b] n = 10
[c] Post-treatment mean value is significantly different from pre-treatment mean value (paired Student's t-test, $p < 0.01$) but not significantly different from normal enamel 71.6 ± 3.1.

TABLE 2

Effect of 5% CPP-ACFP with and without NaOCl pre-conditioning on mineral content of fluorotic enamel

| Treatment | | Specimens | | | | | | | Overall Mean |
|---|---|---|---|---|---|---|---|---|---|
| | | I | II | III | IV | V | VI | VII | |
| Natural fluorotic lesion | ΔZf (vol % min · μm) | 2331 ± 352[a] | —[c] | 3869 ± 70[a] | 2468 ± 323[a] | 2706 ± 103[a] | 3238 ± 194[a] | —[c] | |
| CPP-ACFP treated | ΔZr (vol % min · μm) | 1203 ± 241[a] | —[c] | 1723 ± 262[a] | 1618 ± 427[a] | 1270 ± 596[a] | 2178 ± 216[a] | —[c] | |
| | % M[b] | 48.4 | —[c] | 55.5 | 34.5 | 53.1 | 32.7 | —[c] | 44.8 ± 10.6 |
| Natural fluorotic lesion | ΔZf (vol % min · μm) | 2199 ± 266[a] | 6501 ± 441[a] | —[c] | 1181 ± 261[a] | 2461 ± 213[a] | —[c] | 12048 ± 512[a] | |
| NaOCl/CPP-ACFP treated | ΔZr (vol % min · μm) | 581 ± 230[a] | 471 ± 285[a] | —[c] | 211 ± 137[a] | 552 ± 203[a] | —[c] | 3087 ± 723[a] | |
| | % M[b] | 73.6 | 92.8 | —[c] | 82.1 | 77.6 | —[c] | 74.4 | 80.1 ± 7.8 |

[a] Mean ± SD (n = 6)
[b] % M = percentage mineralization (1 − ΔZr/ΔZf) × 100
[c] Sample lost during processing Black G, McKay F (1916). Mottled teeth—An endemic developmental imperfection of the teeth heretofore unknown in the literature of dentistry. Dent Cosmos 58:129-156.

Commision Internationale de L'Eclaige (1978). Recommendations on uniform colour spaces, colour difference equations and psychometric colour terms. Paris: Bureau Centrale de la DIE Suppl. 2:15.

Den Besten P K, Thariani H (1992). Biological mechanisms of fluorosis and level and timing of systemic exposure to fluoride with respect to fluorosis. J Dent Res 71:1238-43.

Fejerskov O, Baelum V, Manji F, Moller I (1988). Dental Fluorosis—A handbook for health workers Copenhagen: Munksgard.

Fejerskov O, Manji F, Baelum V (1990). The nature and mechanisms of dental fluorosis in man. J Dent Res 69 Spec No: 692-700; discussion 721.

Fejerskov O, Yanagisawa T, Tohda H, Larsen M J, Josephsen K, Mosha H J (1991). Posteruptive changes in human dental fluorosis—a histological and ultrastructural study. Proc Finn Dent Soc 87:607-19.

Fejerskov O, Ekstrand J, Burt B (1996). Fluoride in dentistry. 2nd ed. Copenhagen: Munksgard.

Giambro N J, Prostak K, Den Besten P K (1995). Characterization of fluorosed human enamel by color reflectance, ultrastructure, and elemental composition. Caries Res 29:251-7.

Reynolds E C (1997). Remineralization of enamel subsurface lesions by casein phosphopeptide-stabilized calcium phosphate solutions. J Dent Res 76:1587-95.

Reynolds E C (1998). Anticariogenic complexes of amorphous calcium phosphate stabilized by casein phosphopeptides: a review. Spec Care Dentist 18:8-16.

Reynolds E C, Cai F, Shen P, Walker G D (2003). Retention in plaque and remineralization of enamel lesions by various forms of calcium in a mouthrinse or sugar-free chewing gum. J Dent Res 82:206-11.

Shen P, Cai F, Nowicki A, Vincent J, Reynolds E C (2001). Remineralization of enamel subsurface lesions by sugar-free chewing gum containing casein phosphopeptide-amorphous calcium phosphate. J Dent Res 80:2066-70.

The invention claimed is:

1. A method for reducing white spot lesions on tooth enamel comprising administering a bleach, a protease, or a mixture of proteases to the enamel prior to contacting the enamel with a phosphopeptide-stabilized amorphous calcium phosphate (ACP) and/or amorphous calcium fluoride phosphate (AFCP).

2. A method according to claim 1, wherein the bleach is sodium hypochlorite or a carbamide peroxide bleach.

3. A method according to claim 1, wherein the protease or mixture of proteases comprises a protease selected from the group consisting of endopeptidases, proteinases, exopeptidases, and combinations thereof.

4. A method according to claim 1, wherein the white spot lesion is caused by dental caries, dental erosion or fluorosis.

5. A method according to claim 1, wherein the phosphopeptide is a casein phosphopeptide.

6. A method according to claim 1, wherein the ACP or ACFP is in a basic phase.

7. A kit for the treatment of a white spot lesion including:
(a) a first composition comprising a bleach, a protease or a mixture of proteases; and
(b) a second composition comprising a phosphopeptide-stabilized ACP or ACFP complex in a pharmaceutically acceptable carrier, and
written instructions, wherein the written instructions direct the user to administer the first composition prior to the second composition.

8. A kit according to claim 7, wherein the bleach is sodium hypochlorite or a carbamide peroxide bleach.

9. A kit according to claim 7, wherein the protease or mixture of proteases comprises a protease selected from the group consisting of endopeptidases, proteinases, exopeptidases, and combinations thereof.

10. A kit according to claim 7, wherein the white spot lesion is caused by dental caries, dental erosion or fluorosis.

11. A kit according to claim 7, wherein the phosphopeptide is a casein phosphopeptide.

12. A kit according to claim 7, wherein the ACP or ACFP is in a basic phase.

* * * * *